(12) United States Patent
Anand et al.

(10) Patent No.: US 9,420,988 B2
(45) Date of Patent: Aug. 23, 2016

(54) SYSTEMS AND METHODS FOR TRACKING AND GUIDING HIGH INTENSITY FOCUSED ULTRASOUND BEAMS

(75) Inventors: Ajay Anand, Fishkill, NY (US); John Petruzzello, Carmel, NY (US)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 1297 days.

(21) Appl. No.: 12/809,617
(22) PCT Filed: Dec. 17, 2008
(86) PCT No.: PCT/IB2008/055391
§ 371 (c)(1),
(2), (4) Date: Jun. 21, 2010
(87) PCT Pub. No.: WO2009/081339
PCT Pub. Date: Jul. 2, 2009

(65) Prior Publication Data
US 2010/0274130 A1  Oct. 28, 2010

Related U.S. Application Data

(60) Provisional application No. 61/015,947, filed on Dec. 21, 2007.

(51) Int. Cl.
A61B 8/14 (2006.01)
A61B 8/08 (2006.01)
A61N 7/02 (2006.01)
A61B 8/06 (2006.01)

(52) U.S. Cl.
CPC . *A61B 8/08* (2013.01); *A61N 7/02* (2013.01); *A61B 8/06* (2013.01); *A61B 8/485* (2013.01)

(58) Field of Classification Search
None
See application file for complete search history.

(56) References Cited

U.S. PATENT DOCUMENTS

| | | | |
|---|---|---|---|
| 5,993,389 A | 11/1999 | Driscoll et al. | |
| 6,036,643 A | 3/2000 | Criton et al. | |
| 6,425,867 B1 * | 7/2002 | Vaezy | A61B 8/0833 600/439 |
| 6,488,626 B1 | 12/2002 | Lizzi et al. | |
| 2003/0216648 A1 * | 11/2003 | Lizzi | A61B 8/0858 600/439 |
| 2005/0203399 A1 | 9/2005 | Vaezy et al. | |
| 2005/0215899 A1 | 9/2005 | Trahey et al. | |
| 2005/0228283 A1 * | 10/2005 | Gifford | A61B 8/12 600/459 |
| 2007/0232912 A1 | 10/2007 | Chen et al. | |
| 2008/0097207 A1 | 4/2008 | Cai | |

FOREIGN PATENT DOCUMENTS

| | | |
|---|---|---|
| JP | 2007175509 A | 7/2007 |
| JP | 2007289541 A | 11/2007 |
| WO | 9858588 | 12/1998 |

\* cited by examiner

*Primary Examiner* — Long V Le
*Assistant Examiner* — Bradley Impink

(57) ABSTRACT

The present disclosure provides systems and methods for tracking and guiding high intensity focused ultrasound beams (HIFU). More particularly, the disclosed systems and methods involve use of acoustic radiation force impulse (ARFI) imaging to detect the focal position of an HIFU capable transducer relative to a target area. The focal position may then be 5 compared to a desired treatment location and the orientation and focus of the transducer may be adjusted accordingly so as to reconfigure and/or refocus the HIFU beam relative to the desired treatment location. The desired treatment location may be dynamically determined using bleed detection and localization (BD&L) techniques. Thus, the desired treatment location may be determined using 3D Doppler ultrasound based techniques, wherein changes in quantitative 10 parameters extracted from the Doppler spectra, e.g., Resistance Index (RI), are used to detect and localize a bleeding site for treatment.

12 Claims, 2 Drawing Sheets

SYSTEMS AND METHODS FOR TRACKING AND GUIDING HIGH INTENSITY FOCUSED ULTRASOUND BEAMS

STATEMENT OF GOVERNMENTAL INTEREST

The United States government may hold license and/or other rights to the systems and methods claimed herein. Development of the systems and methods claimed herein was supported by DARPA; Funding Opportunity No. DARPA05-01DBAC.

BACKGROUND

1. Technical Field

The present disclosure relates to high intensity focused ultrasound (HIFU) applications. More particularly, the present disclosure relates to systems and methods for tracking and guiding HIFU beams. Although exemplary embodiments relate primarily to acoustic hemostasis, the disclosed systems and methods apply to and for any HIFU application, including but not limited to HIFU treatments for uterine fibrosis, cancer, and cardiac arrhythmias, such as atrial fibrillation.

2. Background Art

Blood loss from extremity wounds is the number one cause of preventable battlefield death today. In civilian casualties, exsanguinations due to internal bleeding are the most significant cause of death in trauma victims. Hemostatic therapies such as HIFU and electrocautery may be used to quickly stop internal bleeding to prevent onset of progressive and irreversible hemorrhagic shock, which ultimately leads to death. The onset of bleeding must be detected and the site spatially localized in order to treat these trauma wounds effectively. As part of the DARPA DBAC program at Philips Research Briarcliff, 3D Doppler ultrasound based techniques have been developed to detect and localize a bleeding site (herein referred to as "Bleed Detection and Localization" or "BD&L") automatically by tracking the change in quantitative parameters extracted from the Doppler spectra such as Resistance Index (RI). For these emergent care type applications, the device is designed to be operator independent and, therefore, image-based feedback allowing user interaction and control is not available.

Hence, an extremely essential component for success of HIFU based hemostasis treatments is the ability to continually track if the therapy is being delivered at the correct location. Due to tissue heterogeneities and lack of quantitative information on the local thermal and acoustic properties, there exist errors between the intended spatial location of treatment and the actual physical location of the HIFU focus. A tracking and guiding system must, therefore, actively refocus the HIFU beam to the desired location so that the therapy is delivered at the appropriate site without unwanted damage to surrounding normal tissue. Although BD&L techniques may be repeated to determine if a bleed rate has slowed or stopped, these techniques do not provide any quantitative feedback or spatial information relating to the optimal reorientation or refocusing of the therapy relative to the desired treatment location.

A number of researchers have proposed the use of B-mode images to provide imaging feedback and spatially locate the HIFU beam by tracking the presence of hyperechogenicity. However, it has been demonstrated that this information is not always reliable since hyperecho can appear quite some time after the tissue has already been ablated and when the local tissue temperature is close to boiling. The inhomogeneous structure of tissue would make direct B-mode visualization of the focal region of HIFU preceding boiling even more challenging. See B. A. Rabkin, V. Zderic, and S. Vaezy, "Hyperecho in ultrasound images of HIFU therapy: involvement of cavitation," Ultrasound Med Biol, vol. 31, pp. 947-56, 2005. An effective tracking method must be able to locate the HIFU focus without causing any damage to normal tissue.

The following U.S., foreign and PCT patents and publications provide examples of prior art relating to hemostasis and/or HIFU systems. In all cases, the disclosed systems and methods fail to provide adequate means for tracking and guiding therapeutic HIFU beams.

European Patent Publication No. EP0989822 describes a method of producing remote hemostasis within a patient body. The method involves identifying an internal bleeding site and focusing therapeutic ultrasound energy through tissue from a radiation source to coagulate blood adjacent to the site. An imaging transducer provides an image of a portion of a patient body having an internal bleeding site, typically using pulsed Doppler color flow imaging, elasticity imaging, an angiogram or the like. Thus, this patent publication describes a method for effecting hemostasis and the use of ultrasound methods to identify a bleed. In particular, the noted European publication does not describe a method for identifying the location of HIFU focus to ensure treatment of a desired location.

U.S. Patent Publication No. US2005/215899 describes a method for identifying ablated tissue using acoustic radiation force impulse imaging. The disclosed method involves generating acoustic radiation force impulse (ARFI) image data wherein a region of increased stiffness represents ablated tissue. ARFI is thus employed to determine the extent and size of an ablated region. The disclosure does not, however, propose a method of detecting the HIFU focus prior to commencing ablation in order to determine if the ablation will be applied at the desired site. In addition, the sonication for ARFI is not generated using the HIFU transducer.

PCT Publication No. WO2004075987 describes an HIFU delivery method for tracking and accounting for body movement of a subject patient. The disclosed method involves acquiring ultrasound image data of the patient's target area and comparing current image data with previously acquired image data. Discrepancies are analyzed in order to detect and account for patient movement prior to HIFU treatment administration. This patent publication does not involve the use of ARFI. Rather, the disclosure relies on using a sequence of ultrasound images to determine and account for movement. In addition, the disclosed technique does not detect the HIFU beam focus.

U.S. Patent Publication No. US2005/203399 describes an image guided HIFU device for therapy in obstetrics and gynecology. A frame ensures that the alignment between a high intensity focused ultrasound (HIFU) transducer designed for vaginal use and a commercially available ultrasound image probe is maintained, so that the HIFU focus remains in the image plane during HIFU therapy. This patent publication does not propose the use of ARFI to determine the location of the HIFU focus. The proposed mechanical frame is specifically applicable for the transducer geometry in obstetrics and gynecology and cannot be extended for other clinical applications of HIFU. Furthermore, the HIFU focus position is determined only within a 2D plane.

Despite efforts to date, a need remains for systems and methods for effective tracking and guiding HIFU beams.

These and other needs are satisfied by the present disclosure, as will be apparent from the description which follows.

SUMMARY

The present disclosure provides systems and methods for facilitating high intensity focused ultrasound (HIFU). More particularly the present disclosure provides systems and methods that facilitate beam tracking and guidance in HIFU applications.

Generally, the presently disclosed systems and methods involve the use of acoustic radiation force impulse (ARFI) imaging to determine the focal position of an HIFU capable transducer relative to a target area. The focal position may then be compared to a desired treatment location and the orientation and focus of the transducer may be adjusted accordingly so as to direct the HIFU beam relative to the desired treatment location. In exemplary embodiments, ultrasound elasticity imaging-based techniques are used to estimate the focal position of the HIFU beam in real-time. The estimated focal position is compared relative to a desired treatment location. Typically, a processor is used to calculate and adjust the focus and orientation of the transducer so as to optimally direct the HIFU beam relative to the desired treatment location.

Ultrasound elasticity-based techniques, such as Acoustic Radiation Force Impulse (ARFI) imaging, may be used to determine the focal position. See, e.g., K. Nightingale, R. Bentley, and G. Trahey, "Observations of tissue response to acoustic radiation force: opportunities for imaging," *Ultrason Imaging*, vol. 24, pp. 129-38, 2002; K. Nightingale, M. S. Soo, R. Nightingale, and G. Trahey, "Acoustic radiation force impulse imaging: in vivo demonstration of clinical feasibility," *Ultrasound Med Biol*, vol. 28, pp. 227-35, 2002. In exemplary embodiments involving ARFI imaging, the transducer induces a radiation force relative to a target area, e.g., using and/or based upon low power sonication. The focal position may be determined by detecting the point of maximum tissue displacement following the radiation force.

In general, the systems and methods disclosed, as related to tracking and guiding of an HIFU beam, may be implemented before HIFU therapy commences. Thus, the disclosed systems and methods advantageously facilitate focusing of an HIFU beam relative to a treatment location, while minimizing collateral damage to surrounding tissue. In exemplary embodiments "Bleed Detection and Localization" (BD&L) techniques may be used to detect and localize a desired treatment location. Thus, HIFU beam tracking and beam focusing steps may be cyclically interleaved with BD&L and HIFU beam administration to continuously ensure that HIFU therapy is being delivered to the desired treatment location.

The disclosed systems and methods have broad-based applications and offer many advantages over prior art as discussed in the present disclosure. Additional features, functions and benefits of the disclosed systems and methods will be apparent from the description which follows, particularly when read in conjunction with the appended figures.

BRIEF DESCRIPTION OF THE DRAWINGS

To assist those of ordinary skill in the art in making and using the disclosed systems and methods, reference is made to the appended figures, wherein.

DESCRIPTION OF EXEMPLARY EMBODIMENT(S)

Advantageous systems and methods for facilitating High Intensity Focused Ultrasound (HIFU) are provided according to the present disclosure. In general, systems disclosed herein include (i) an HIFU capable transducer, (ii) a diagnostic imaging probe, and (iii) a processor. The disclosed methods typically involve determining the focal position of an HIFU capable transducer and associated tracking/guidance steps/functionalities.

According to the present disclosure, acoustic radiation force impulse (ARFI) imaging may be used to detect the focal position for an HIFU capable transducer relative to a target area. In exemplary embodiments, the diagnostic imaging probe is used to probe a target area and obtain imaging data before and after inducement of a radiation force relative to the target area. The radiation force is typically induced using the HIFU capable transducer, e.g., using low power sonication. The radiation force causes motion of the target area and the region of greatest tissue displacement represents the focal position of the transducer. Thus, in exemplary embodiments, the imaging data is compared and/or analyzed using the processor to determine the focal position for the HIFU capable transducer relative to a target area.

After the focal position of the HIFU capable transducer is detected, the orientation and/or focus of the transducer may be adjusted such that a new/adjusted focal position substantially matches a desired treatment location. In exemplary embodiments, the focal position of the transducer is continuously detected and adjusted so as to dynamically track and guide the HIFU beam relative to a desired treatment location and/or treatment path. Generally, treatment using the HIFU beam, e.g., administration of high power sonication, will not commence until the detected focal position substantially matches a desired treatment location, thereby reducing the risk of harm to surrounding tissues.

In exemplary embodiments, the desired treatment location may be dynamically determined using BD&L techniques. Thus, in exemplary embodiments, the desired treatment location is determined using 3D Doppler ultrasound based techniques, wherein changes in quantitative parameters extracted from the Doppler spectra, e.g., Resistance Index (RI), are used to detect and localize a bleeding site for treatment. In general, other detection and localization techniques may by employed instead of or in conjunction with BD&L in order to determine the desired treatment area.

Figure 1:
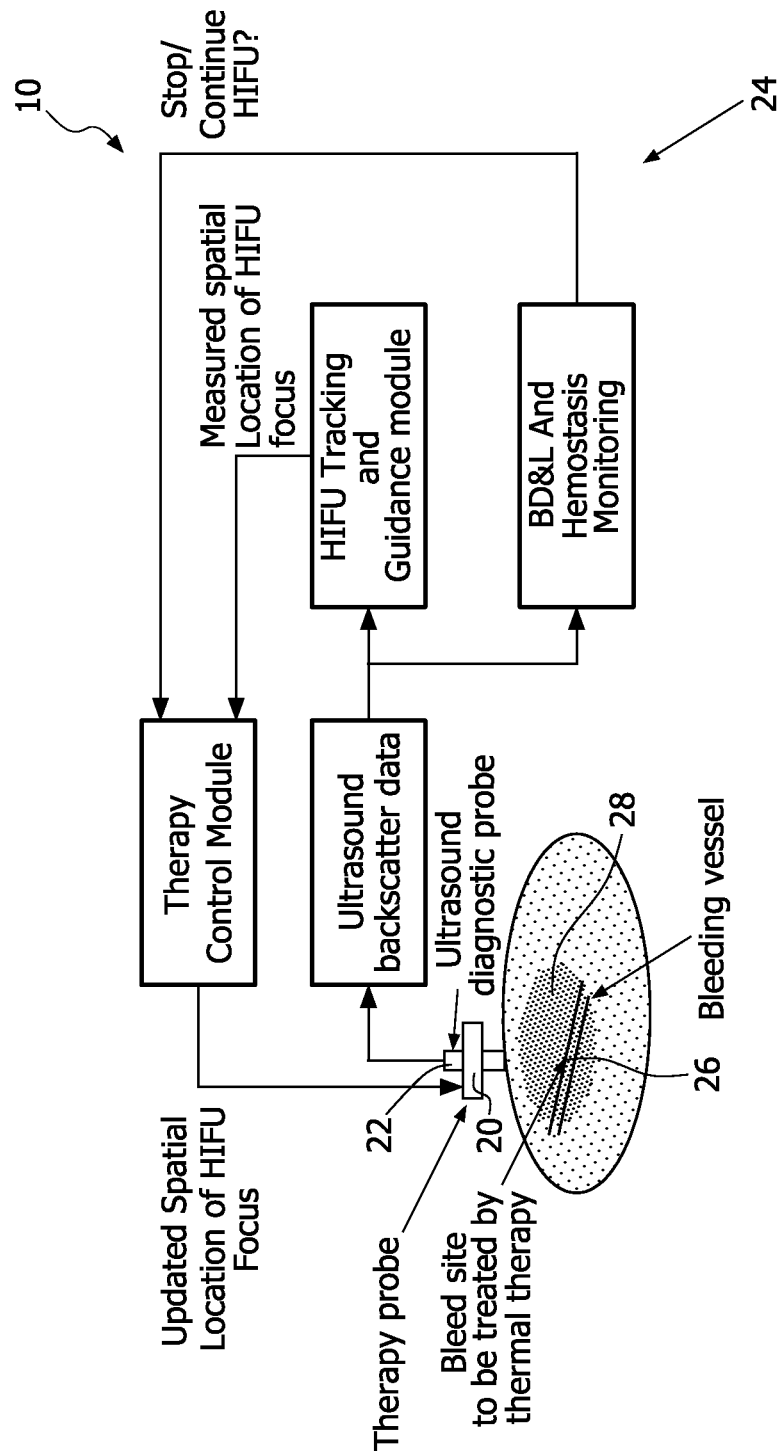
FIG. 1 is a block diagram of an exemplary high intensity focused ultrasound (HIFU) system for hemostasis according to the present disclosure.

With reference now to FIG. 1, an exemplary HIFU system 10 for inducing hemostasis is depicted. The system includes an HIFU capable transducer 20, a diagnostic imaging probe 22, and a processor 24. The transducer 20 and probe 22 are positioned relative to a target area 28. The target area 28 may generally be determined by a rough initial assessment of an injury.

After the transducer 20 and probe 22 are positioned relative to the target area 28, BD&L techniques may be used to detect the spatial location of the bleed site (the desired treatment location 26). In general, the desired treatment location 26 is detected using 3D Doppler spectra analysis. Sonication for producing the Doppler effect may be provided by the transducer 20. Data for the spectra analysis is obtained by the probe 22 and analyzed by the processor 24.

Once the desired treatment location 26 is determined, the focal position for the transducer 20 may be detected using ultrasound elasticity techniques, such as ARFI imaging. In exemplary embodiments, diagnostic level tracking pulses are applied relative to the target area 28 and a first set of backscatter data is obtained for use as a reference. After the reference backscatter data is obtained, low power sonication is applied using the transducer 20 relative to the target area 28. The low power sonication induces a radiation force relative to the target area 28 which causes tissue displacement. In alternative embodiments, the probe 22 may also be used to induce the radiation force, alone or in conjunction with the transducer 20. After the radiation force has caused tissue displacement, a second set of tracking pulses may be applied relative to the target area 28 and a second set of backscatter data may be obtained. The processor 24 is used to compare and analyze the first and second sets of backscatter data to determine the focal position of the transducer 20. The focal position of the transducer 20 corresponds to the point of maximum tissue displacement.

After the focal position of the transducer 20 has been determined, the processor 24 adjusts the orientation and/or focus of the transducer 20, such that the new focal position substantially matches the desired treatment location 26. Thus, the HIFU beam focus is configured to coincide with the bleed site determined using BD&L techniques.

Figure 2:
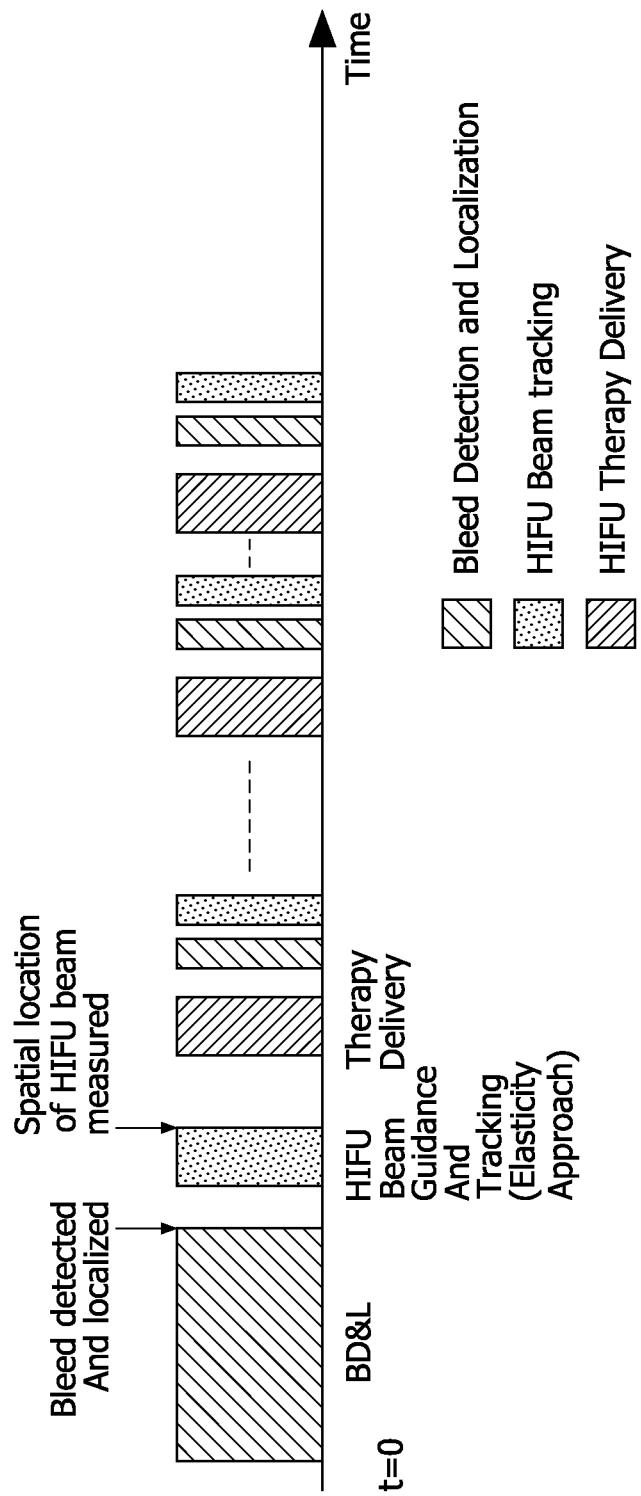
FIG. 2 is an exemplary time sequence representation for using the HIFU system of FIG. 1.

FIG. 2 depicts an exemplary time sequence for using the system 10 of FIG. 1. In exemplary embodiments, BD&L and/or tracking/guiding techniques may be cyclically repeated to create a dynamically self-correcting system. Thus, HIFU beam therapy delivery may, periodically, be interrupted, e.g., in order to ensure the correct orientation and/or focus of the transducer. The BD&L technique may also be used to track the bleed rate and determine if the rate has diminished or stopped. In exemplary embodiments, a non-diminishing bleed rate may indicate that the HIFU beam is incorrectly focused or simply ineffective. Thus, the processor may stop HIFU therapy if a diminishing bleed rate is not detected over a certain period time. If HIFU therapy is stopped because of a non-diminishing bleed rate, tracking and guiding techniques may be applied to reorient and/or refocus the transducer before treatment recommences.

Thus, the disclosed systems and methods provide may be advantageously employed in various high intensity focused ultrasound (HIFU) applications. The disclosed systems and methods facilitate tracking and guiding of HIFU beams relative to a target region and/or target path. The disclosed systems/methods have wide ranging applicability, including acoustic hemostasis techniques, treatment of uterine fibrosis, cancer treatment and arterial fibrillation treatments.

Although the present disclosure has been described with reference to exemplary embodiments and implementations thereof, the disclosed systems and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

What is claimed is:

1. A system for facilitating administration of a High Intensity Focused Ultrasound (HIFU) beam relative to a target area, the system comprising;

a. a HIFU capable transducer;
   b. a diagnostic imaging probe; and
   c. a processor in communication with the HIFU capable transducer and diagnostic imaging probe, wherein the processor, HIFU capable transducer, and diagnostic imaging probe are configured to perform the processes of (i) dynamically determining a desired treatment location of the target area, wherein the step of dynamically determining includes detecting and localizing a site for treatment using 3D Doppler ultrasound based techniques, and (ii) cyclically repeating a tracking and guiding of a HIFU beam therapy before the HIFU beam therapy commences and recommences to create a dynamically self-correcting system, the tracking and guiding being applied to reorient and refocus the HIFU capable transducer, and wherein the diagnostic imaging probe is adapted to obtain a first set of imaging data for the target area, wherein the HIFU capable transducer is adapted to induce a radiation force relative to the target area using low power sonication, wherein the diagnostic imaging probe is further adapted to obtain a second set of imaging data for the target area after the radiation force has been induced, and wherein the processor is adapted to compare the first and second sets of imaging data to determine a focal position for the HIFU capable transducer relative to the target area, the processor further adapted to adjust an orientation and focus of the HIFU capable transducer such that the adjusted orientation and focus of a new focal position of the HIFU capable transducer substantially matches the desired dynamically determined treatment location of the target area.

2. The system of claim 1, wherein the HIFU capable transducer is adapted to treat hemostasis.

3. The system of claim 1, wherein the 3D Doppler ultrasound based techniques comprise bleed detection and localization (BD&L) techniques used to determine the desired treatment location.

4. The system of claim 1, wherein the first and second sets of imaging data are obtained by detecting backscatter from a respective first and second tracking pulse provided by the HIFU capable transducer.

5. The system of claim 1, wherein the processor further determines focal position by analyzing detected backscatter using cross-correlation and time-delay estimation techniques.

6. The system of claim 1, wherein the processor further determines focal position as a region of the target area exhibiting maximum tissue displacement.

7. The system of claim 1, wherein the HIFU capable transducer is further adapted to treat the target area with high power sonication.

8. A method for facilitating administration of a high intensity focused ultrasound (HIFU) beam relative to a target area, the method comprising:

(i) dynamically determining, via (a) a HIFU capable transducer, (b) a diagnostic imaging probe, and (c) a processor, a desired treatment location, wherein dynamically determining includes detecting and localizing a site for treatment using 3D Doppler ultrasound based techniques, and (ii) cyclically repeating a tracking and guiding of a HIFU beam therapy before the HIFU beam therapy commences and recommences to create a dynamically self-correcting method, the tracking and guiding being applied to reorient and refocus the HIFU capable transducer, and a. probing, via the diagnostic imaging probe, the target area for a first set of imaging data;
b. inducing a radiation force relative to the target area using a low power sonication from the HIFU capable transducer;
c. probing, via the diagnostic imaging probe, the target area for a second set of imaging data;
d. comparing, via the processor, the first set of imaging data to the second set of imaging data in order to determine a focal position for the HIFU capable transducer relative to the target area; and
e. treating the target area with a high power sonication from the transducer, the method further comprising adjusting, via the processor, an orientation and focus of the HIFU capable transducer such that the adjusted orientation and focus of a new focal position of the HIFU capable transducer substantially matches the desired dynamically determined treatment location of the target area.

9. The method of claim 8, wherein the HIFU capable transducer is used to treat hemostasis.

10. The method of claim 8, wherein the 3D Doppler ultrasound based techniques comprise bleed detection and localization (BD&L) techniques.

11. The method of claim 8, wherein the steps of dynamically determining, cyclically repeating, probing, inducing, probing, comparing, and treating are repeated until treatment is no longer necessary.

12. The method of claim 11, wherein bleed detection and localization (BD&L) techniques are used to determine when treatment is no longer necessary.

* * * * *